United States Patent [19]

Hsu et al.

[11] Patent Number: 5,922,961
[45] Date of Patent: Jul. 13, 1999

[54] TIME AND POLARIZATION RESOLVED ACOUSTIC MICROSCOPE

[75] Inventors: Nelson N. Hsu, Gaithersburg, Md.; Dan Xiang, Beijing, China; Gerald V. Blessing, Frederick, Md.

[73] Assignee: The United States of America as represented by the Secretary of Commerce, Washington, D.C.

[21] Appl. No.: 08/644,161

[22] Filed: May 10, 1996

[51] Int. Cl.⁶ .......................... G01N 29/22; G01N 29/06
[52] U.S. Cl. .............................................. 73/606; 310/336
[58] Field of Search ........................... 73/606, 607, 608, 73/602, 620, 627, 629, 632, 642, 644; 310/334, 335, 336, 337, 321, 322, 326, 327, 367, 368, 369

[56] References Cited

U.S. PATENT DOCUMENTS

| | | | |
|---|---|---|---|
| 2,989,864 | 6/1961 | Bamford | 73/620 |
| 3,968,680 | 7/1976 | Vopilkin et al. | 73/602 |
| 4,213,344 | 7/1980 | Rose | 73/620 |
| 4,510,810 | 4/1985 | Kanda et al. | 73/606 |
| 4,523,122 | 6/1985 | Tone et al. | 73/644 |
| 4,535,630 | 8/1985 | Samodovitz | 73/642 |
| 4,541,281 | 9/1985 | Chubachi et al. | 73/606 |
| 4,566,333 | 1/1986 | Chubachi et al. | 73/642 |
| 4,577,504 | 3/1986 | Kanda et al. | 73/606 |
| 4,597,293 | 7/1986 | Kanda et al. | 73/606 |
| 4,603,585 | 8/1986 | Atalar | 73/606 |
| 4,655,083 | 4/1987 | Chubachi | 73/606 |
| 4,683,751 | 8/1987 | Imade et al. | 73/606 |
| 4,694,699 | 9/1987 | Cheeke | 73/606 |
| 4,969,361 | 11/1990 | Kawasaki et al. | 73/593 |
| 5,001,674 | 3/1991 | Kawasaki | 73/640 |
| 5,056,368 | 10/1991 | Kawasaki et al. | 73/640 |
| 5,195,372 | 3/1993 | Fushimi et al. | 73/593 |
| 5,211,059 | 5/1993 | Hayakawa et al. | 73/606 |
| 5,307,680 | 5/1994 | Drescher-Krasicka | 73/606 |
| 5,349,862 | 9/1994 | Chubachi et al. | 73/602 |

*Primary Examiner*—Hezron Williams
*Assistant Examiner*—Rose M. Miller
*Attorney, Agent, or Firm*—Larson & Taylor

[57] ABSTRACT

An acoustic microscope system is provided for analyzing the properties of a solid sample with fluid coupling. The system includes a transducer comprising a curved active piezoelectric element and an insulating backing member having a curved surface on which the piezoelectric element is mounted, a casing for backing member, and electrical input/output leads connected to the piezoelectric element. A pulser receiver, connected to the leads of the transducer, generates coherent test pulses of short duration and receives echoes from the solid sample resulting from these pulses and having a received echo waveform comprising multiple arrivals including direct reflection from the interface between the fluid and the solid sample. A wave recorder records the received echo waveform so as to enable the determination therefrom of information relating to the characteristics of the solid sample.

10 Claims, 2 Drawing Sheets

TIME AND POLARIZATION RESOLVED ACOUSTIC MICROSCOPE

BACKGROUND OF THE INVENTION

1. Field of the Invention

The present invention relates to ultrasonic microscope systems used in the analysis of the properties of solid samples and, more particularly, to an improved acoustic microscope system.

2. The Prior Art

A well known acoustic microscope employed by many researchers uses a cylindrical lens in a "V(z)" scan technique, wherein V(z) represents the voltage amplitude of the transducer output signal as a function of the normal distance, i.e., the distance measured along the z axis, between the transducer and the sample being analyzed. This technique or approach, hereinafter referred to as the Kushibiki system, is discussed, for example, in Jun-Ichi Kushibiki and Noriyoshi Chubachi, "Material Characterization by Line-Focus-Beam Acoustic Microscope," IEEE Trans. on Sonics and Ultrasonics, Vol. SU-32, No. 2, 189–211, March 1985, and is the basis of at least one commercial acoustic microscope system, viz., the Honda AMS 5000 Ultrasonic Measuring System. In the system discussed in the cited reference, the transducer includes a polished sapphire lens having a concave cylindrical front surface. The active piezoelectric element, i.e., the element which converts elastic changes into an electrical output as a receiver, and converts electrical input into elastic wave motion as a transmitter, is a flat ZnO film provided on the back side of the lens. The transducer is operated in a burst continuous wave (CW) mode. The most important measurement made by this system is that of the scan distance z. More specifically, in this method, precise z distance control and measurement are necessary in order to determine the distance between two maxima or minima in the V(z) curve (i.e., the plot of V as a function of distance z) and to compute the speed using the known CW frequency. The signal processing used is a gated voltage measurement made as the transducer is moved in the z-direction. Fourier transforms are necessary to convert the V(z) curve into the desired velocity values.

Patents in the field which were of interest include the following: U.S. Pat. No. 4,510,810 (Kanda et al.); U.S. Pat. No. 4,541,281 (Chubachi et al.); U.S. Pat. No. 4,566,333 (Chubachi et al.); 4,577,504 (Kanda et al.); U.S. Pat. No. 4,597,293 (Kanda et al.); U.S. Pat. No. 4,603,585 (Atalar); U.S. Pat. No. 4,655,083 (Chubachi); U.S. Pat. No. 4,694,699 (Cheeke); U.S. Pat. No. 5,211,059 (Hayakawa et al.); U.S. Pat. No. 5,307,680 (Drescher-Krasicka); and U.S. Pat. No. 5,349,862 (Chubachi et al.).

Briefly considering these references, the Kanda et al. ('810) patent discloses an ultrasonic microscope which uses a flat piezoelectric element located on top of an acoustic lens. The Chubachi et al. ('281 & '333) patents discloses an ultrasonic microscope system which uses a flat piezoelectric element disposed over a curved acoustic lens. The Kanda et al. ('504) patent discloses an ultrasonic transducer with a piezoelectric element disposed over an acoustic lens. The Kanda et al. ('293) patent discloses mounting a piezoelectric element on the concave bottom surface of a substrate such that the piezoelectric element is likewise curved in shape. The Atalar patent discloses a flat piezoelectric element mounted on top of an acoustic lens. The Chubachi ('083) patent discloses dual transducers with piezoelectric elements located on top of acoustic lenses. The Cheeke patent discloses an acoustic microscope transducer comprising a cylindrical lens with a piezoelectric element mounted on top of the lens. The Hayakawa et al. patent discloses an acoustic microscope transducer comprising multiple piezoelectric elements mounted on the bottom curved portion of an acoustic lens. The Drescher-Krasicka patent discloses an acoustic microscope transducer which utilizes a curved acoustic lens. The Chubachi et al. '862 patent discloses an ultrasonic microscope in which circular shaped piezoelectric elements are mounted on the flat top of an acoustic lens.

SUMMARY OF THE INVENTION

In accordance with the invention, an ultrasonic transducer is provided which generates and receives short-duration ultrasonic pulses through a fluid in order to analyze or probe a solid sample which is submerged in the fluid. The transducer has a curved front surface comprising a thin piezoelectric active element and includes a backing member or element comprising a heavily damped solid which is impedance-matched to the piezoelectric active element.

The transducer is preferably connected to a pulser-receiver operated in a pulse-echo mode wherein an echo is received from a solid sample responsive to the generation, and transmission through the fluid, of a pulse by the transducer. The received echo waveform, which is a voltage as a function of time, will show multiple arrivals. These arrivals can be identified as follows: (i) direct reflection from the fluid/solid sample interface; (ii) a surface skimming longitudinal head wave; (iii) a surface skimming shear head wave; (iv) an interface wave commonly referred to as the leaky surface wave; and (v) back reflection from the back surface of the sample. (It is noted that the names Rayleigh, Scholte and Sezawa have sometimes been assigned to the leaky surface wave.) Directionally-polarized wave speeds can be determined based on these arrivals alone and, knowing the density of the solid sample, the localized elastic properties of the solid sample can then be computed from these wave speeds.

In accordance with a further feature of the invention, by moving the transducer along the normal axis, i.e., the z-axis, of the surface of the solid sample, multiple traces of the echo waveform can be displayed as a projected three dimensional plot commonly known as a "waterfall" plot. Using this plot, the arrivals can be precisely delineated and the wave signals evaluated with high precision. By rotating the transducer about this same normal axis, the wave speed information in different directions on the surface is obtained, thereby enabling the anisotropic elastic properties of the solid to be determined. In addition, local surface roughness, surface flows, and sub-surface flows together with thickness variations and the nature of the coating materials, if any, will also affect the appearance of the echo waveforms. As a consequence, these waveforms can be analyzed by comparison with the corresponding waveforms obtained from smooth, flawless reference samples. Images of various elastic and surface/sub-surface properties of the solid as well as derived elastic or surface properties can be obtained by scanning the solid sample with the transducer disposed at a fixed distance from the surface of the sample.

Comparing the acoustic microscope system of the invention with the Kushibiki system described above, the present invention uses a curved piezoelectric element to produce a coherent short duration wave pulse originating from a curved surface, in contrast with the Kushibiki system wherein the active piezoelectric element is a flat (ZnO) film on the back side of a lens and the transducer is operated in a burst CW mode as noted above. Thus, one principle difference between the two systems is similar to the difference between a lens and a mirror in providing optical focusing. In this regard, similarly to the advantages of a mirror over a lens in optical focusing, the transducer of the invention provides a large aperture at low cost. Moreover, the present invention uses a wide bandwidth, short duration transient pulse mode operation which resolves the successive echo arrivals in time. As a result, the time delays between the initiation of the generating electrical pulse and the various echo arrivals can be determined with a single test configuration. In the testing or analyzing method of the invention, the most important measurement is that of the time interval, with the z-direction scan serving to enhance the precision of this time measurement. This contrasts with the Kushibiki system wherein the most important measurement is the scan distance z which, as explained above, must be precisely measured and controlled.

A further advantage of the present invention over the Kushibiki system is that the instrumentation requirements for the pulsed ultrasonic testing of the invention are significantly less than for the burst CW mode employed in the Kushibiki system. For example, both the cost of the instrumentation and the power required to drive the transducer are less for a pulsed system than for a burst CW system.

The difference in the signal processing used in the two systems is also significant. In accordance with the present invention, a direct time-interval measurement of the echo waveform is used whereas, as mentioned hereinabove, in the Kushibiki system, a gated voltage measurement is used as the transducer is moved in the z-direction, with subsequent Fourier transforms being required to convert the V(z) curve into the desired velocity values.

Other features and advantages of the invention will be set forth in, or apparent from, the following detailed description of preferred embodiments of the invention.

DESCRIPTION OF THE PREFERRED EMBODIMENT

Figure 1:
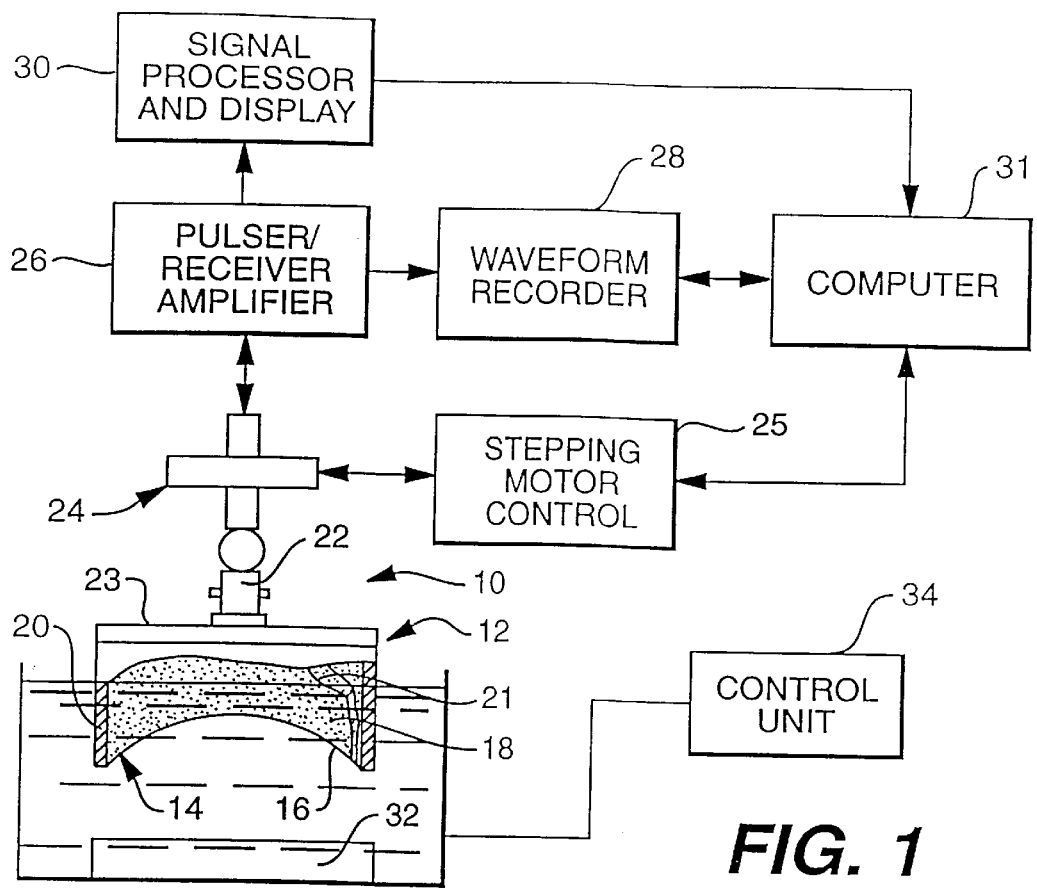
FIG. 1 is a schematic representation, partially broken away and partially in block diagram form, of an acoustic microscope system constructed in accordance with a preferred embodiment of the invention.

Referring to FIG. 1, a preferred embodiment of the acoustic microscope system of the invention is shown. The system, which is generally denoted 10, includes a transducer 12 which is partially broken away for illustrative purposes. Transducer 12 includes a curved face 14 which, in manufacture is shaped by a cylindrical mandrel, and to which, in this embodiment, is applied a polyvinylidene di-fluoride (PVDF) film 16 in the shape of a rectangle having the dimensions 30 mm×12 mm×0.025 mm thick in a specific implementation. The film has coated electrodes on both surfaces. The film is deposited on a backing element 18 which comprises, in the specific example under consideration, a tungsten power loaded epoxy material.

The backing element 18 is encased in a casing or housing 20 formed by a rectangular metal tube. The tube formed casing 20 is machined with one end flat and the other curved. The tungsten loaded epoxy forming backing element 18 is cast from the top to fill the cavity formed with the casing 20 as the sides and the film 16 as the bottom. Electrical leads or insulated wires 21 embedded (cast) in the backing element 18 connect the PVDF film to the transducer input/output connector or terminals indicated at 22 (such as a BNC) mounted on a back plate 23. The latter serves as the back cover and can provide the necessary support in a testing assembly as well. In a non-limiting example, the focal length of the transducer 12 is 25 mm and the aperture thereof is 28.2 mm.

A conventional scanning unit or scanner 24 provides scanning of the transducer 12 as discussed in more detail below. A stepping motor 25 controls movement for scanner 24 in a conventional manner. Output connector 22 is connected (through scanner 24 in the illustrated embodiment) to a pulser/receiver amplifier 26 the amplifier section of which provides a 20 or 40 dB gain. The output signal from pulser/receiver amplifier 26 is recorded by a waveform recorder 28 such as a digital oscilloscope. A signal processor and display unit 30 can also be provided which processes the output signal from pulser/receiver amplifier 26 and displays the results of this signal processing in other formats. A computer 31 controls stepping motor 25 and performs the analysis/processing. It will be appreciated that the particular control and signal processing/display units illustrated in the block diagram are merely exemplary and that, for example, computer 31 and waveform recorder 28 could completely replace signal processor and display unit 30. Also, in an alternative embodiment, a mechanical control unit indicated at 34 can provide the required movement of a sample 32 relative to the transducer 12.

Figure 2:
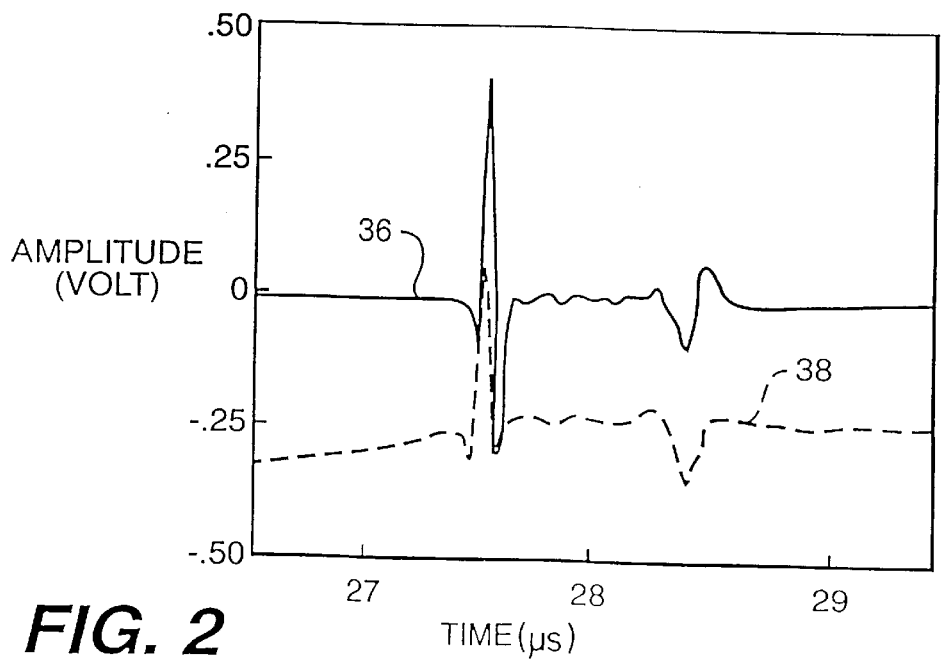
FIG. 2 is a plot of amplitude versus time, depicting echoes received in response to an excitation pulse and comparing experiment with theory.

In operation, in accordance with one aspect of the invention, movement of the test sample 32 relative to transducer 12 is provided by control unit 34 and the resultant waveform recorded. Referring to FIG. 2, there is shown the resultant experimentally recorded waveform as recorded by the waveform recorder 28. In particular, for the specific waveform shown, a sample 32 in the form of a glass plate in a fluid (water) was moved from the focal point of transducer 12 to a point closer to the transducer. In FIG. 2, which is a plot of amplitude versus time for a glass sample, corresponding to sample 32, located 5.5 mm inside of the focal point of the transducer 12, the experimentally recorded waveform is denoted 36, while a theoretically computed waveform is indicated in dashed lines at 38.

In the waveforms of FIG. 2, the first pulse is the direct reflected echo from the water/glass interface, the second pulse is the surface skimming longitudinal head wave, and the third pulse is the (dilated) interface wave. For the particular test configuration under consideration, the surface skimming shear head wave is not clearly present. The simulated or theoretical waveform 38 is based on a three dimensional Green's function, a curved line transducer and an assumed ricker wavelet as the source waveform. In FIG. 2, the horizontal axis indicates the time in microseconds ($\mu s$) measured from the initial trigger of the electrical pulse which excites the transducer 12. It will be appreciated that knowing the speed of the acoustic wave in water, a determination can be made of the location along the z-axis of transducer 12, and thence the longitudinal and interface wave speeds without any length measurements or other physical measurements. In this regard, reference is made to N. N. Hsu, D. Xiang, S. E. Fick and G. V. Blessing, "Time and Polarization Resolved Ultrasonic Measurements Using a Lensless Line-Focus Transducer," 1995 IEEE International Ultrasonics symposium (November 1995), which is hereby incorporated by reference.

Figure 3:
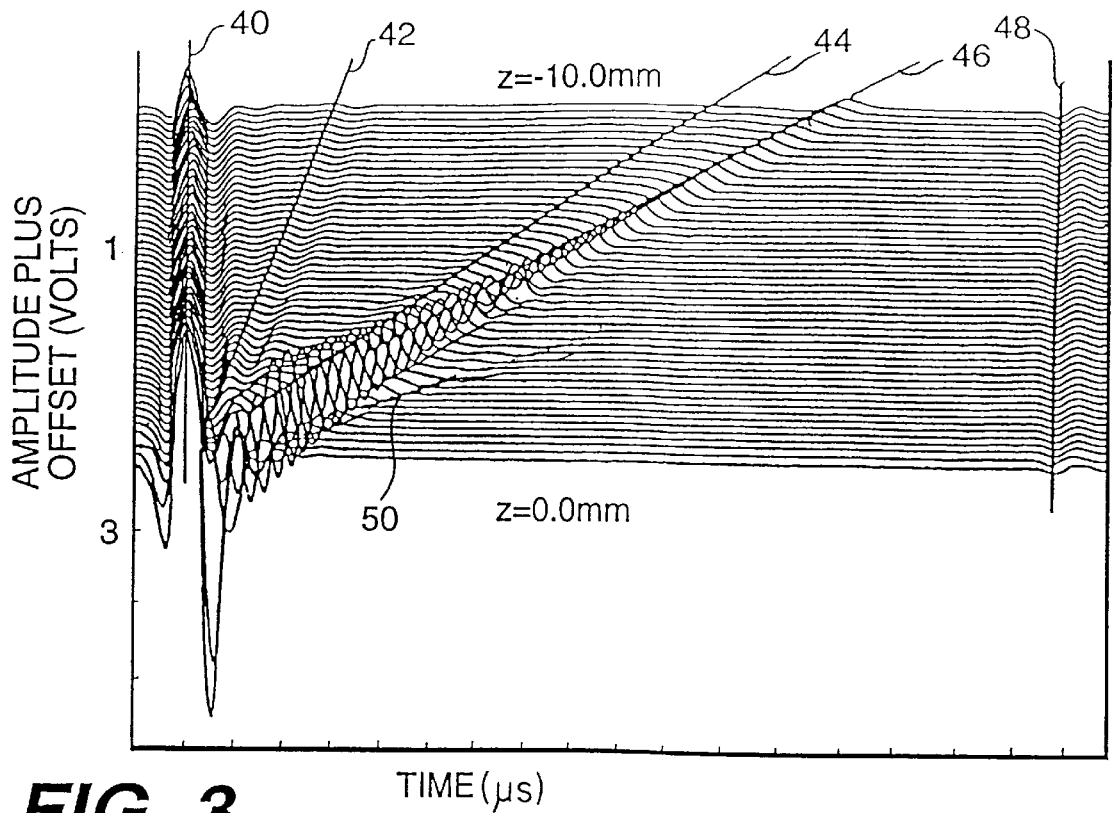
FIG. 3 is a "waterfall" plot of a Z-scanned echo waveform wherein the direct reflection is used as the reference trigger in time.

Referring to FIG. 3, the multiple time wave traces of the waveforms, obtained by moving the transducer closer to the sample, are staggered and are patterned on the same graph with incremental offsets, so as to enable the arrival times of the corresponding waves to be determined with high precision. In FIG. 3, which is a so-called "waterfall" plot of the Z-scanned echo waveform between Z=0.0 mm to Z=10.0 mm, the front surface center reflected wave is denoted 40, the skimming longitudinal wave is denoted 42, the skimming shear wave is denoted 44, the interface wave is denoted 46, the back surface reflection is denoted 48 and the front surface edge reflected wave is denoted 50. In connection with FIG. 3, the first direct reflected waves were used to trigger the oscilloscope employed as waveform recorder 28, and, therefore, these waves appear virtually aligned at the initial reference time thereof and all of the other arrivals are relative to this time.

For the plot of FIG. 3, the sample was a SiC reinforced aluminum plate of 6.50 mm thickness and, on the right side of FIG. 3, the arrivals from the back side of the sample are shown at 48. These arrivals occur at a fixed time delay with respect to the front reflected echo and are, therefore, also vertically aligned, as shown. The amount of this time delay between the vertically aligned echoes shown at 40 and 48 can also be used to compute the longitudinal wave speed of the sample material.

Figure 4:
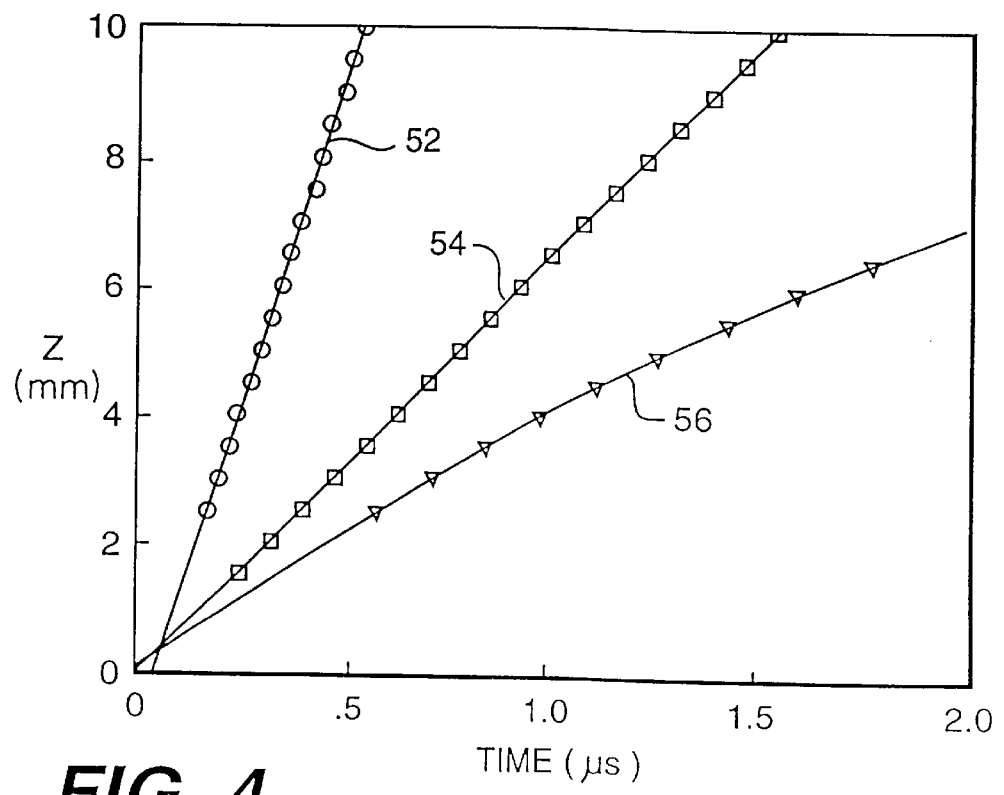
FIG. 4 is a plot of distance versus time (Z-T curve) for the test results obtained with a glass sample.

Referring to FIG. 4, there are shown the data of arrival times of various wave fronts and the fitting curves that have been determined using simple algorithms for a testing relative to a glass sample. In FIG. 4, which is essentially a plot of distance Z versus time T, the longitudinal skimming wave is indicated at 52, interface wave at 54 and the front surface edge reflected at wave 56. The least-squares-fitting curves (shown by 52, 54 and 56) can be respectively represented as follows: $Z=19.5\ T-0.562$; $Z=6.41\ T+0.0370$; and $Z=0.498\ T^2+4.48\ T+0.119$. The wave speeds can be precisely computed from the two linear slopes (fitting-curves 52 and 54 with relative standard deviations of 0.848% and 0.186% respectively) shown in FIG. 4. As expected, the edge-reflected wave arrival is, as shown by curve 56, nonlinear with respect to time.

In an exemplary, non-limiting embodiment, the device has a wave path length on the order of 1 mm and a time resolution of 1 ns. For most engineering materials evaluation, this can be considered as "local," and the synthetic images of elastic property variation over a given sample area can be constructed by performing a simple x-y scan of the transducer 12 over the area of interest.

Although acoustic microscopes have many potential applications, they are, in general, expensive and difficult to operate and because of this, can only be used in research laboratories in limited applications. In contrast, because of the simplicity and ease of use thereof, the present invention reduces the complexity of operation of an acoustic microscope device to that of an ordinary A-scan or C-scan device such as have been used throughout industry.

Among the many useful applications of the present invention are the following: nondestructive materials evaluation, i.e., elastic constants determination, surface and sub-surface flaw detection, surface texture (topography) and residual stress measurement, and sample dimensions, as applied to metal and alloys, ceramic materials and coatings, semiconductors (the raw or intermediate product), plastics, composite materials, functionally gradient materials, and medical and biological materials.

It is noted that while the embodiments described above are generally preferred, variations in, and/or additions to, these embodiments can provide further advantages. For example, the active element of the transducer can be formed by separated or split arcs, i.e, a circular arc with a central position removed, or by simply two or more parallel arcs, or multiple segments in a phased array, but still with a solid backing and with electrical connections as in the single-ended unit. Further, the unit can be made to be portable and means can be provided to align the transducer kinematically in a direction normal or orthogonal to the sample surface. In addition, means can be provided to provide vertical scanning and in an angular direction around the z-axis. Also, a coupling liquid can be provided between the sample and the transducer, rather than providing total submersion of the sample.

Although the present invention has been described relative to specific exemplary embodiments thereof, it will be understood by those skilled in the art that variations and modifications can be effected in these exemplary embodiments without departing from the scope and spirit of the invention.

What is claimed is:

1. An acoustic microscope system for analyzing the properties of a fluid coupled solid sample in a fluid in direct alignment with the system, said system comprising:

a transducer comprising a curved active piezoelectric element and an insulating backing member having a cylindrical surface on which said piezoelectric element is mounted and to which said piezoelectric element conforms, a casing for backing member, and electrical output leads connected to said active piezoelectric element, said backing member being impedance matched to said piezoelectric element, and said piezoelectric element comprising an elongate piezoelectric film of a finite width and a length extending in an arc transversely of the cylindrical surface of the backing member to define a transducer aperture, said transducer having a focal length smaller than said transducer aperture;

pulser and receiver means connected to said output leads for generating a coherent test pulse of short time duration and receiving echoes from the solid sample resulting from said pulse and having a received echo waveform comprising multiple arrivals including direct reflection from the interface between the fluid and the solid sample; and wave recorder means for recording the received echo waveform so as to enable the determination therefrom of information relating to the characteristics of the solid sample.

2. An acoustic microscope system as claimed in claim 1 wherein said pulser and receiver means comprises a pulser-receiver amplifier.

3. An acoustic microscope system as claimed in claim 1 further comprising scanning means for varying the relative distance between the solid sample and the transducer.

4. An acoustic microscope system as claimed in claim 3, wherein said scanning means comprises means for moving the sample.

5. An acoustic microscope system as claimed in claim 3, wherein said scanning means comprises means for moving the transducer.

6. An acoustic microscope system as claimed in claim 1, wherein said active piezoelectric element comprises a polyvinylidene di-fluoride film.

7. An acoustic microscope system as claimed in claim 6, wherein electrodes are coated on opposite surfaces of said film.

8. An acoustic microscope system as claimed in claim 6, wherein said backing member comprises a tungsten powder loaded epoxy member.

9. An acoustic microscope system as claimed in claim 8, wherein said casing includes a removable back cover through which the epoxy of the epoxy member can be cast.

10. An acoustic microscope system as claimed in claim 1, wherein said casing includes an open rectangular housing in which said backing member is dispersed and having a front and a back, a cover plate being positioned at the back of the housing and said active element being positioned at the front of the housing, an input/output connector being mounted on said cover plate, and said output leads extending through said backing member to said input/output connector on said cover plate.

* * * * *